(12) United States Patent
Kwirandt

(10) Patent No.: US 7,057,718 B2
(45) Date of Patent: Jun. 6, 2006

(54) DEVICE AND METHOD FOR INSPECTING THE TRANSPARENT BOTTOMS OF BOTTLES

(75) Inventor: Rainer Kwirandt, Obertraubling (DE)

(73) Assignee: Krones AG, Neutraubling (DE)

( * ) Notice: Subject to any disclaimer, the term of this patent is extended or adjusted under 35 U.S.C. 154(b) by 159 days.

(21) Appl. No.: 10/297,909

(22) PCT Filed: Jul. 4, 2002

(86) PCT No.: PCT/EP02/07403

§ 371 (c)(1),
(2), (4) Date: Dec. 11, 2002

(87) PCT Pub. No.: WO03/006970

PCT Pub. Date: Jan. 23, 2003

(65) Prior Publication Data

US 2003/0142299 A1    Jul. 31, 2003

(30) Foreign Application Priority Data

Jul. 12, 2001    (DE) .................................. 101 33 104

(51) Int. Cl.
*G01N 21/00* (2006.01)

(52) U.S. Cl. .............................. 356/239.5; 250/223 B; 356/426; 356/239.4; 356/239.6

(58) Field of Classification Search ............. 356/239.1, 356/239.4, 239.5, 239.6, 240.1; 250/223 B
See application file for complete search history.

(56) References Cited

U.S. PATENT DOCUMENTS

| | | | |
|---|---|---|---|
| 3,770,969 A | * | 11/1973 | Ansevin et al. ......... 250/223 B |
| 4,249,075 A | * | 2/1981 | Lovalenti ................. 250/223 B |
| 4,270,863 A | * | 6/1981 | Trogdon ....................... 356/71 |
| 4,746,212 A | * | 5/1988 | Sudo et al. ............. 250/223 B |
| 4,908,507 A | * | 3/1990 | Imre et al. .............. 250/223 B |
| 4,910,406 A | * | 3/1990 | Craig et al. ................. 250/372 |
| 4,914,289 A | * | 4/1990 | Nguyen et al. ......... 250/223 B |
| 4,943,713 A | | 7/1990 | Yoshida |
| 5,926,268 A | * | 7/1999 | Bonewitz et al. ........ 356/240.1 |
| 6,072,575 A | * | 6/2000 | Loll ........................ 356/239.4 |
| 6,275,603 B1 | * | 8/2001 | Cronshaw et al. ...... 250/223 B |

FOREIGN PATENT DOCUMENTS

| | | |
|---|---|---|
| DE | 3839682 A1 | 6/1989 |
| EP | 045407 | 7/1981 |
| EP | 0045407 A1 | 2/1982 |
| EP | 0403496 B1 | 8/1994 |
| EP | JP2000193606 | 7/2000 |
| JP | JP04118546 | 4/1992 |
| JP | 04-270951 A * | 9/1992 |

(Continued)

*Primary Examiner*—Layla G. Lauchman
*Assistant Examiner*—Juan D. Valentin, II
(74) *Attorney, Agent, or Firm*—Marshall, Gerstein & Borun LLP

(57) ABSTRACT

A method and a device of inspection of the transparent bottom of a bottle or similar item by using an optical system which shows the bottom of the bottle, for recording by a camera, in front of a surface which is illuminated by an illumination device, and the surface being located at a distance from the bottom of the bottle, whereby foreign bodies in the bottle can be detected. The illuminated surface can be the liquid level surface in the bottle, the bottom of foam in the bottle, or the bottom of the bottle closure member. The surface in the bottle can be illuminated from below or above the bottle.

28 Claims, 2 Drawing Sheets

FOREIGN PATENT DOCUMENTS

| | | | |
|---|---|---|---|
| JP | 06-034573 A * | 8/1994 | |
| JP | 06-034574 A * | 8/1994 | |
| JP | 8075674 | 3/1996 | |
| WO | WO 97/14956 | 4/1997 | |
| WO | WO 98/19150 | 5/1998 | |
| WO | WO 98/45690 | 10/1998 | |

* cited by examiner

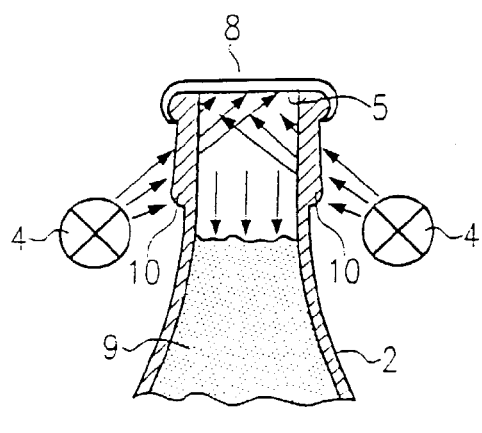
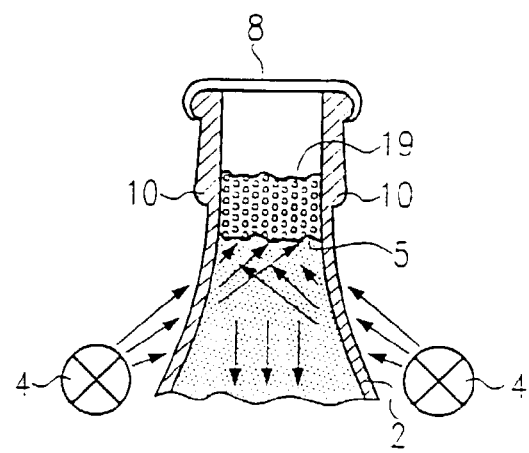
FIG.2a    FIG.2b
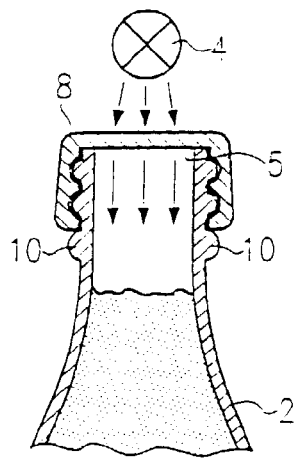
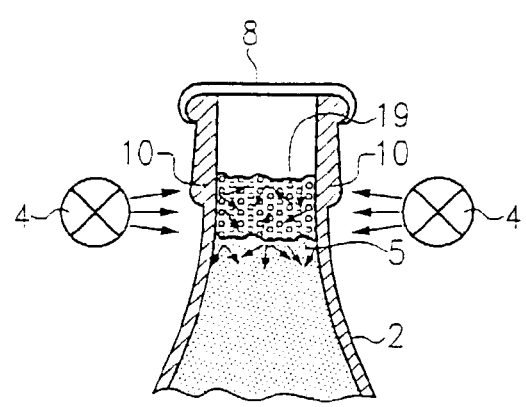
FIG.2c    FIG.2d
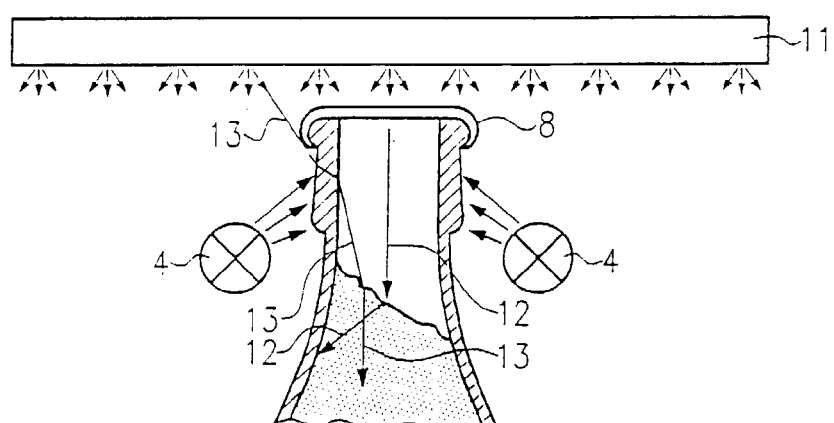
FIG.3

DEVICE AND METHOD FOR INSPECTING THE TRANSPARENT BOTTOMS OF BOTTLES

CROSS-REFERENCE TO RELATED APPLICATIONS

This disclosure is the U.S. national stage, under 35 U.S.C. § 371, of International Application No. PCT/EP02/07403, having an international filing date of Jul. 4, 2002, and claims priority to Germany Application No. 101 33 104.5, filed Jul. 12, 2001.

FIELD OF THE INVENTION

The invention relates to a device for inspection of transparent bottoms of bottles or similar items, with an optical system which presents a camera for recording at least one image of the bottom of the bottle and an illumination device, as well as to a method for inspecting the floor of bottles or similar items in which at least one image of a transparent bottom of a bottle is recorded with a camera.

BACKGROUND OF THE INVENTION

From JP 08075674A a device is known for recognizing foreign bodies in a transparent container which is already filled and closed, where light sources which are located laterally next to the bottom of the container illuminate the container and a camera which is arranged below the bottom of the bottle records the light which is reflected by the foreign bodies.

A drawback of such a known device is that the camera not only acquires the transparent bottom of a container, but the entire container from inside, resulting in strong contrast differences in the image area. Consequently, an electronic evaluation of the images, which is usually based on differences in brightness, is made difficult.

SUMMARY OF THE INVENTION

An object of the present disclosure is to provide a device and method of inspection of bottoms of bottles or similar items, by means of which the bottom of a bottle or similar item can be examined for the presence of foreign objects, soiling, etc., and the foreign bodies can easily be recognized, for example by electronic evaluation.

This object is achieved by a device for inspection of a transparent bottom of a closed bottle, or of a bottle substantially filled with a liquid, in order to detect foreign bodies contained in such a bottle. At least one illumination device is also provided, which illuminates a side of a surface facing the bottom of the bottle from outside through a side wall of the bottle, which surface is either part of a closure of the bottle or part of a liquid level of the liquid substantially filling the bottle. A camera is also provided for recording light reflected by the surface to the bottom and passing through the bottom, to obtain at least one image of the bottom of the bottle.

In the bottom inspector according to the present disclosure, the surface which is illuminated by an illumination device functions as background, from which foreign bodies clearly stand out as visible shadows.

It is advantageous to record an image of at least the entire bottom of the bottle. However, according to the invention, it is also possible to record only a part of the bottom area.

In an advantageous alternate embodiment of the present disclosure, the bottom inspector is provided for the inspection of filled and/or closed bottles. It is precisely in the case of bottles which are filled or closed that one can only with great difficulty view the bottom from the top with the foreign body in the bottle. This difficulty is due to the refraction and the light absorption of the filling product or the bottom closure. It is precisely in this context that the bottom inspector according to the invention is advantageous.

In another particularly advantageous variant of the present disclosure, the illuminated surface is optically diffuse. This means that light which is incident on the illuminated surface is scattered, at least in part, in a large spatial angular range. Because the illuminated surface is optically diffuse, a background which appears homogeneous is formed for recording the bottom of the bottle.

In a further alternate embodiment of this disclosure, the illuminated surface includes a surface consisting of the bottom side of the closure of a bottle and/or the surface of the filling product of a bottle and/or the bottom side of a foam head of a liquid which is contained in a bottle. Such surfaces in or near the bottle are at a distance from the bottom of the bottle, so that the illuminated surface is not sharply shown for the camera. As a result, the background for the recording of the bottom of the bottle optically appears very homogeneous, and fails to present large differences in intensity, even if the illuminated surface itself presents certain differences in brightness.

Moreover, it is advantageous if an optical device is provided which optically magnifies the illuminated surface for the recording. Indeed, this also makes it possible to use comparatively small surfaces as background for the recording of relatively large bottle bottoms.

The optical device can advantageously be a lens and, in particular, a Fresnel lens, which is arranged between the bottom of the bottle and the camera. Fresnel lenses have the advantage of being lightweight and inexpensive.

If the Fresnel lens is arranged so that the illuminated surface substantially lies within, or a small a distance behind, the focal plan of the Fresnel lens, then the illuminated surface appears to be very blurred, and as a result, the contours of the illuminated surface are not negative for image recording. Because the background is represented as blurred, it appears very homogeneous in its light intensity.

In the determination of the focal plane, one must take into account that a large portion of the ray path is located in an optical medium (body of the bottle, liquid) which has an index of refraction different from 1. Because the light refracts as it enters and exits the medium on the interface surface, the focal plane is not at the focal length of the lens as it was determined in light.

In yet another advantageous variant of the present disclosure, the camera is arranged in such a manner that, in the case of an upright bottle, an image can be recorded below the bottle position, and the illuminated surface is located above the bottom of the bottle. As a result, it is possible to arrange the camera relatively close to the bottom of the bottle, so that, using a large spatial angle, a large image of the bottom of the bottle can be generated, without having to use expensive magnification optics (for example zoom lenses). In this manner, the illuminated surface is advantageously above the bottom of the bottle, so that the light passes from the illuminated surface through the bottom of the bottle and is incident on the camera.

An advantageous embodiment is one where the illuminated surface is illuminated from at least two sides to achieve a regular illumination of the illuminated surface, which is advantageous for a homogeneous background of the image.

An advantageous arrangement of the illumination device is one where the light is emitted substantially at an angle and upward. As a result, the horizontally oriented light surface can be optimally illuminated.

An alternate embodiment of the disclosure includes providing the illumination device so that the light is emitted substantially at an angle and downward or downward onto the illuminated surface. Using this arrangement one can also obtain an optical illumination of the surface in the case of a horizontal light surface.

In another particularly advantageous embodiment of the disclosure, an additional illumination device is provided, which is arranged above the bottle and which emits light in the direction of the bottle. With such an arrangement it is possible to compensate for dark areas in the background representation, which are the result of a slanted or moving liquid surface in the bottle.

In another advantageous embodiment, feed and removal devices are provided with the bottom inspector, which feed and remove bottles, so that in a relatively rapid succession, several bottles can be inspected continuously, one after the other. For this purpose, a conveyor can be provided which transports the bottles through the inspection position. In the process, only the area of the bottle which is used for beaming in the light and the bottom area must be remain uncovered. For this purpose, a conveyor is available in which the bottle is held between laterally contacting elements, for example a clamping belt pair: of a conveyor.

For the inspection of several bottles at a high production rate, it is also advantageous to provide an evaluation installation by means of which the images recorded can be electronically evaluated in a fully automated manner to determine whether foreign bodies are present in the bottle and, for example, which is applied against the interior of the bottom of the bottle. For this purpose, it is particularly advantageous to use an electronic camera, such as, for example, CCD camera (color, black and white), because the images which have been recorded can thus be transmitted directly to the evaluation device.

By focusing the camera on the volume area of the bottle, it is also possible to examine the liquid in the bottle. For this purpose, it is possible, for example, to detect and analyze bubbles, turbidities, suspended substances, etc.

The illumination device can comprise incandescent lamps, radiators, light diodes, lasers, laser diodes, flash light lamps, halogen lamps, gas discharge lamps or similar items. If needed, the illumination device can be briefly switched on by means of an appropriate control device, even if only for a short time period, for recording the image.

The method according to the disclosure provides for the recording of an image of the bottom of the bottle with a camera, where the bottom of the bottle, for the recording, is shown in front of a surface which is illuminated by an illumination device. As a result of the representation of the bottom of the bottle in front of an illuminated background it is possible, due to the formation of shadows, to detect foreign bodies in the area of the bottom of the bottle.

A particularly advantageous embodiment of the method consists in inspecting filled and/or closed bottles. Since, in the case of such bottles, it is not possible to view the bottom of the bottle from the top, that is through the neck of the bottle, the method can be carried particularly advantageously with such bottles.

Another particularly advantageous embodiment of the method utilizes diffusely scattered light which is incident on the illuminated surface. Consequently, it is not crucially important what the direction is of the light which is incident on the illuminated surface, and the choice of the direction of incidence of the light on the illuminated surface is thus not of crucial importance.

An additional advantageous variant is the use, as the illuminated surface, of the bottom side of the bottle closure, the surface of the liquid and/or the bottom side of a foam head of a liquid contained in the bottle. All such surfaces are suitable as illuminated background for recording the bottom of the bottle. Since such surfaces as a rule are at a great distance from the bottom of the bottle, such surfaces as a rule appear blurred during the recording of the bottom of the bottle, which is regulated so it appears sharp, or of objects located on the bottom of the bottle, so that a background with homogeneous appearance is formed. This homogeneous background is particularly advantageous if the images are to be evaluated electronically to determine contrasts, because, as a result of the blurred representation of the illuminated surface, the latter generally presents no contrast or only very little contrast.

An advantageous embodiment involves using a closure with a bright bottom side. Such a bright bottom side of the closure can scatter a particularly large amount of light, resulting in a good light yield for recording the image.

A particularly advantageous variant of the methods of this disclosure consists in providing an optical device, by means of which the illuminated surface can be optically magnified for recording the image. As a result it is possible to use as the illuminated surface even surfaces which are small compared to the bottom, such as, for example, the internal side of a crown cap or a screw closure of a bottle.

An additional advantageous embodiment of the method according to the present disclosure includes recording the image of the bottom of the bottle through a lens, and in this context, in particular through a Fresnel lens, with a camera. However, such a Fresnel lens, on the one hand, magnifies the image of the bottom of the bottle only slightly, and, on the other hand, it can be used to magnify the illuminated surface, and thus, even illuminated surfaces which are small compared to the bottom of the bottle can be used as illuminated background surfaces.

A further advantageous embodiment of the method of the present disclosure involves placing the illuminated surfaces substantially in or a short distance behind the focal plane of the Fresnel lens. By such an arrangement, the illuminated surface is recorded by the camera substantially blurred, so that any contrasts and structures of the illuminated surface are represented in a washed out manner, resulting in a homogeneous background for the recording of the image, which is advantageous for recognizing foreign objects in the bottle.

Furthermore, an additional embodiment includes recording the image from below the bottom of a bottle. As a result, it is possible to have direct access to the bottom of a bottle to record the image. It is also advantageous that the illuminated surface is located above the bottom of the bottle. As a result, the bottom of the bottle can be recorded from immediately below with the illuminated surface as background.

It is also advantageous to illuminate the illuminated surface from at least two sides, because, in that manner, an even illumination of the illuminated surface is achieved.

Furthermore, it is advantageous to use bottles which have a flange below their closure device, because such a flange clearly simplifies the coupling of light in the area of the bottom side of the closure. The reason for this is that such a flange deflects light, as does a lens, and directs it to the bottom side of the closure.

Furthermore, it is advantageous to illuminate the illuminated surface substantially at an angle from below. For a horizontally arranged surface, one can thus guarantee an optical illumination of the surface. In particular, if the surface is located on a nontransparent object, it is advantageous to illuminate the surface from below, if the image is to be recorded from below.

Furthermore, an advantageous method includes illuminating the illuminated surface substantially at an angle from above or from above. If the surface is located on a part which at least partially transmits light, for example foam in the bottle or a light transmitting closure, one can thus guarantee a good homogeneous illumination of the illuminated surface.

A particularly advantageous variant of the method according to the disclosure includes illuminating the bottle with an additional illumination device from above. If, as a result of the slanted surface of liquid in the bottle, the light is deflected by the illuminated surface from its direction toward the camera, or if it is refracted, then, in this state of a slanted surface of liquid, the light which is incident on the bottle, laterally past the closure, is refracted by the slanted surface in the direction of the camera. As a result, dark fields which form in the illuminated background can be compensated, at least in part.

Another advantageous method is one in which the recorded images are electronically evaluated and in which the bottles are fed and removed to and from a bottom inspection device, respectively, which carries out the method according to the invention. As a result it is possible to inspect a multitude of bottles successively and at short time intervals.

In the following, embodiments of the device and the method according to the disclosure are explained with reference to the drawing figures.

BRIEF DESCRIPTION OF THE DRAWINGS

FIGS. 2a–2d show alternate embodiments in schematic detail representations, and FIG. 3 shows an additional advantageous embodiment in a schematic representation.

DETAILED DESCRIPTION OF THE INVENTION

Figure 1:
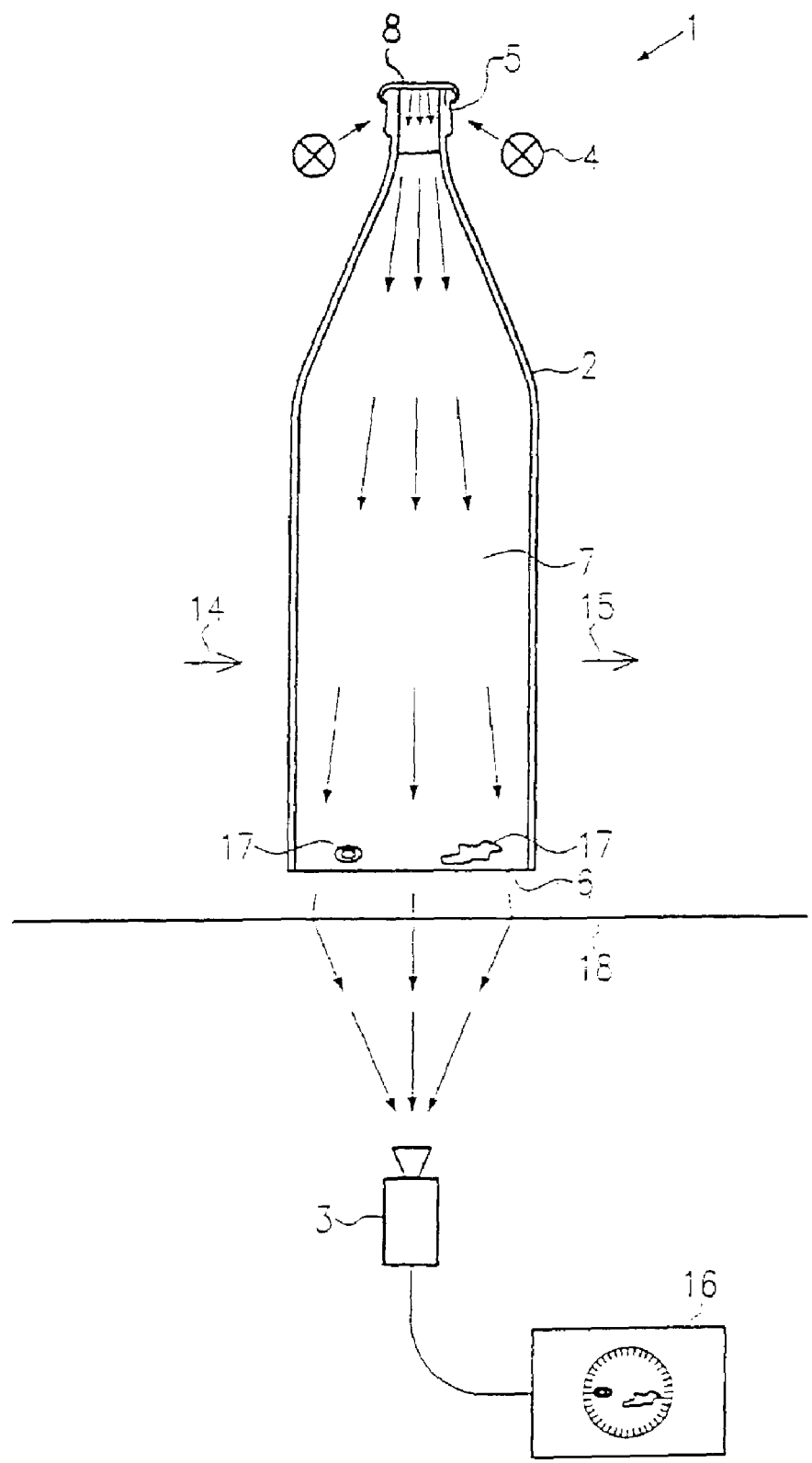
FIG. 1 shows a bottom inspector according to the present disclosure in a schematic view.

FIG. 1 represents a bottom inspector 1, by means of which a transparent glass or plastic bottle 2 can be inspected. Any foreign bodies 17 which may be located in a filled and already-closed bottle 2 are to be detected In the upper area of the bottle, in proximity to the neck of the bottle, illumination devices 4 are provided, which illuminate the bottom side 5 of a closure 8. The light which is scattered by the bottom side 5 of the closure propagates at least partially downward in the direction toward the bottom of the bottle. There, the light is deflected or absorbed by any foreign body 17 present, so that they cast shadows. Then the light exits through the light transmitting bottom 6 of the bottle and it is collimated by a Fresnel lens 18 in a direction toward a camera 3. The camera 3 now records an image of the bottom 6 of the bottle, together with any foreign bodies 17 present. Here the camera is focused on the area of the bottom, 6, of the bottle. The recorded image is electronically analyzed by an electronic evaluation installation 16.

By focusing a camera on the volume or on the bulging area 7 of the bottle 2, the liquid can be examined for turbidity, suspended or other particles, and also for bubbles, etc.

The result of the evaluation is used to remove by sorting bottles, and to exclude them from further use, if foreign bodies are detected in any bottle.

As a result of the arrangement of the Fresnel lens 8, camera 3 has a field of vision in which the bottom side 5 of the bottle closure 8, which is illuminated by the illumination devices 4, appears as a bright background. The objects 17, which are located in the light path between the illuminated surface 5 and the camera 3, are thus detected as shadows.

In FIGS. 2a–2d, special variants of the illuminated surface 5 and its illumination are represented.

In FIG. 2a, the top part of a bottle 2 with a filling product 9 is represented. The illumination devices 4, which are arranged laterally next to the neck of the bottle, emit light at least partially or predominantly, in the direction toward the internal side 5 of a crown cap 8. In this context, the flanges 10 on the neck of the bottle are particularly helpful, as they act as a kind of lens and thus they can deflect the light of the illumination devices 4 onto the surface 5 to be illuminated. On the bright internal side 5 of the crown cap 8, the light is diffusedly scattered and its spreads at least partially downward, as indicted by the three parallel arrows, in the direction of the filled product 9. As a result of passing through the filled product and the bottom of the bottle, the light is recorded by camera 3 (FIG. 1). This variant of the illuminated surface 5 is particularly suitable for filled products 9, which do not tend to form foam, or for bottles in which the filled product produces no foam.

If foam 19 is located in the bottled 2 (FIG. 2b), the foam bottom side 5 of the foam head can be used as illuminated surface. Again, illumination devices 4 are provided next to the bottle and they illuminate the foam bottom side 5 at an angle from below. Since the foam bottom side 5 also diffusely scatters light, at least a part of the light is deflected downward in the direction toward the camera 3. Using this light, the bottom inspection can be advantageously carried out.

In FIG. 2c, an additional possible arrangement of the optical system of the device according to the invention is represented. For example, if a closure 8 is used, which transmits light, at least in part or slightly, as can be achieved, for example with plastic bottle closures, then the illuminated surface 5, which again represents the bottom side of the closure 8, can also be illuminated from above, that is through the closure. In this case, the illumination unit 4 can advantageously be applied above the closure 8. Alternately, or additionally, it is also conceivable to use such closures to illuminate, similarly to the representation of FIG. 2a, the bottom side 5 of the closure 8 from below. In this context, the flanges 10 could again be advantageously used for deflecting light.

The illumination of the illuminated surface from above (FIG. 2c) is not limited to a screw closure, as represented in FIG. 2c, rather it merely depends on whether the closure 8 at least partially transmits light.

In FIG. 2d, another possibility is represented, in which the illuminated surface 5 consists of the top side of the filled product 9 or the bottom side of the foam 19. For example, if the foam 19 is a white or light colored foam, there is a possibility of radiating light from the illumination devices 4 horizontally into the foam area 19. The light is repeatedly diffusely reflected in the foam area 19 and finally it exits, at least in part, downward in the direction toward the bottom of the bottle. In this manner it is also possible to generate the illuminated surface 5, which serves as background for the bottom inspection.

In FIG. 3, a particularly advantageous embodiment is represented, which is particularly relevant if the surface of the liquid in the bottle 2 is in motion and, for example, slanted. In FIG. 3, the entire surface of the liquid is represented in the slanted position, however, the following explanations also apply to the case where only a part of the liquid level is slanted, or when different parts of the surface of the liquid are slanted at different angles. The fact that the surface of the liquid is slanted can be the result of a slanted position on the bottle or of acceleration, deceleration or movement of the bottle along a circular path. Simple shaking of the bottle during transport by the inspection device can also result, for a short period, in: the formation of waves on the surface of the liquid in the bottle.

As represented in FIG. 3, the light which is radiated from the illumination units 4 onto the closure 8 and from there radiated approximately vertically downward (see arrow 12), is refracted by the slanted surface of the liquid away from the direction toward the bottom of the bottle, 6, and toward the camera. From the point of view of the camera this means that the illuminated surface 5 which should here be the bottom side of the closure 8 is no longer visible for the camera, at least in part. As a result, the bottom side of the closure 8 can no longer serve in its entirety as an illuminated surface, in front of which the bottom of the bottle is to be recorded.

However, this can be compensated by providing, above the bottle 2 (as represented in FIG. 3), an additional illumination device 11, whose light is then coupled when the surface of the liquid is slanted in the direction toward the bottom 6 of the bottle 2. As represented in FIG. 3, as a result of the slanted position of the surface of the liquid, the light of the light beam 13 is refracted vertically downward in the direction toward the bottom. In cases where the surface of the liquid is substantially horizontal, the light of the light beam 13 is refracted in another direction, so that it substantially does not reach the camera. The light of the additional illumination device 11 is thus visible from the position of the camera only if the surface of the liquid is in motion or slanted in some areas or overall. By coupling the light of the additional illumination device 11 in the area in which the surface of the liquid is slanted, the loss of light, which was sent out of the bottom side of the closure 8 in the direction toward the bottom of the bottle, is at least partially or completely compensated for. Then any dark areas in the background illumination, which form as a result of the slanted position of the surface of the liquid or wave formation on the surface of the liquid, are prevented or compensated for.

It is also conceivable to use a device in which the surface of the liquid is intentionally slanted in the bottle to thus omit the illumination devices 4 and to work only with the additional illumination device 11.

A method according to the invention will now be explained with reference to the device represented in the figures.

As shown in FIG. 1, light is refracted onto the surface to be illuminated by means of an illumination device 4. On this surface 5, the light is scattered and thus refracted toward the bottom of the bottle. With camera 3, a recording of the bottom 6 or of foreign bodies 17, located in the proximity of the bottom, is then made. Here the illuminated surface 5 serves as bright background, so that the foreign bodies 17 are represented by dark contours or shadows. Consequently, such foreign bodies 17 can easily be detected. With the Fresnel lens 18, the bottom of the bottle, 6, with a foreign body 17, is then shown in front of the surface 5 which is illuminated with the illumination device 4. The image obtained with the camera 3 is then evaluated by means of an evaluation installation 16, as represented in FIG. 1. Such an evaluation installation conducts a predetermined image recognition or it compares the images obtained with reference images to reach a conclusion concerning the presence of foreign bodies 17 in the bottle 2.

The bottles represented in FIGS. 1–3 are in each case filled and closed with closure 8. As a result of the closing of the bottle, it is relatively simple to produce an illuminated surface 5, because the closures 8, with their bright, usually white bottom side, make available an appropriate surface. Here the surface 5 must be only slightly diffuse—a condition which is met by nearly all conventional crown cap bottom sides—so that the light which is incident at an angle on the bottom side of the closure 8 scatters at least in part in the direction toward the bottom of the bottle.

In the method according to the present disclosure, as shown in FIGS. 2a–2d, the bottom side 5 of the closure 8 as well as the bottom side 5 of a foam area 19 can be used. The bottom side 5 of a closure can be illuminated in the case of a nontransparent closure 8 from below, and in the case of a transparent closure 8 from below and also from above.

As a result of the recording of the image with a camera 3 through the Fresnel lens 18, the illuminated surface 5 now has the appearance of a highly magnified canvas, in front of which the foreign bodies 17 clearly stand out. The illuminated surface 5 for recording an image is thus optically magnified by the Fresnel lens 18.

Furthermore, as shown in FIG. 1, in a variant of this method, the bottles are transported in a direction 14 to a bottom inspector 1 and then removed, in a direction 15, from this bottom inspector. This process can be carried out by conveyor belts (not shown) which are opposite in position, and which engage the bottles laterally, continuously and at a high speed. The recording of the image 3 can be triggered by the bottle itself in an appropriate manner, as soon as the bottle 2 is in an appropriate position for image recording. During the recording, the bottle 2 can be advantageously held or transported by a conveyor. As a result, the bottles can be transported to and removed from the inspection position. The conveyor is advantageously such that the bottom area transmits light so that the bottom area can be easily photographed.

If the bottles 2 are moved in direction 14 and 15, the illumination devices 4 represented in FIG. 1 must be located laterally with respect to the bottles, viewed in the direction of motion.

The method is advantageously carried out with two light sources, which are arranged in an appropriate manner around the neck of the bottle, however, it is also possible to use more or fewer light sources.

As shown in FIG. 2a, the flange 10 is used for the purpose of deflecting the light from the illumination device 4 in the direction toward the bottom side 5 of the closure 8.

A particularly advantageous variant of the method according to the present disclosure consists in illuminating the bottle from above with an additional illumination device 11. As a result, dark fields which form in the area of the image of the background 5 during the recording of the image as a result of a liquid surface which is at least partially slanted in the bottle 2, are compensated for. In the process, the light which is incident on the closure 8, laterally past the margin of the bottle 2, is refracted into the bottle, where it encounters the slanted surface of the liquid, which then refracts the light downward in the direction toward the bottom of the bottle. As a result, if the surface of the liquid is slanted, the light of the additional illumination device 11 is coupled in the beam path to the bottom 6 and the camera 3. This compensates for the loss of light which occurs due to the slanted surface of the liquid because the light is refracted from the beam path to the bottom 6 and the camera.

I claim:

1. A device for inspection of a transparent bottom of a bottle which is at least one of closed or substantially filled with a liquid, for detection of foreign bodies contained in the bottle, comprising:
    a surface (5), said surface being at least one of part of a closure of the bottle, part of a liquid level of the liquid substantially filling the bottle, or a bottom side of a foam head of a liquid contained in the bottle;
    at least one illumination device, said illumination device illuminating a bottom side of the surface, said bottom side of the surface being a side of the surface facing the bottom of the bottle, from outside through a side wall of the bottle; and
    a camera for recording light reflected by the surface to the bottom and passing through the bottom, to obtain at least one image of the bottom of the bottle.

2. Device (1) according to claim 1, wherein the illuminated surface (5) is optically diffuse.

3. Device (1) according to claim 1, and an optical installation (18) is provided which optically magnifies the illuminated surface (5) for the recording.

4. Device (1) according to claim 3, wherein the optical installation (18) is a lens (18) which is provided between the bottom of the bottle (6) and camera (3).

5. Device (1) according to claim 4, wherein the lens (18) is arranged in such a manner that the illuminated surface (5) is located one of substantially in or a small distance behind the focal plane of the lens (18).

6. Device (1) according to claim 1, wherein the camera is arranged in such a manner that, if the bottle is vertical, an image can be recorded from below the bottle position, and the illuminated surface (5) is located above the bottom of the bottle (6).

7. Device (1) according to claim 1, wherein the illuminated surface (5) is illuminated from at least two sides.

8. Device (1) according to claim 1, wherein the illumination device (4) emits light substantially at an angle and upward.

9. Device (1) according to claim 1, wherein above the bottle (2), an additional illumination device (11) is provided, which radiates light in the direction toward the bottle (2).

10. Device (1) according to claim 1, wherein a feed device and a removal device are provided for continuous feeding and removing of bottles to and from the inspection device (1).

11. Device (1) according to claim 1, and an evaluation installation (16) is provided for the electronic evaluation of the recorded image.

12. Device according to claim 1, wherein the bottle has a closure (8) thereon while the bottle is being inspected by the device for inspection, the closure having a closure bottom side against which detectable shadows are cast by any objects located in a light path between the closure bottom side and the camera.

13. Device according to claim 1, wherein the bottle (2) has a closure device thereon while the bottle is being inspected by the device for inspection, and the bottle further having a flange (10) disposed under its closure device.

14. Device (1) according to claim 4, wherein the lens (18) is a Fresnel lens.

15. Device (1) according to claim 9, wherein the additional illumination device (11) radiates light in the direction of the bottle shoulder area.

16. Method for the inspection of transparent bottoms of bottles, comprising:
    exposing the bottom of the bottle to a bottom side of a surface in front of which an image may be projected, said surface being located at a distance above the bottom of the bottle;
    illuminating the bottom side of the surface using an illumination device so as to project an image in front of the surface, said illumination device being positioned such that the projected image includes light reflected by at least one of part of a closure of the bottle, part of a liquid level of the liquid substantially filling the bottle, or a bottom side of a foam head of a liquid contained in the bottle; and
    recording at least one image of the bottom of the bottle using a camera.

17. Method according to claim 16, and inspecting the bottle.

18. Method according to claim 16, wherein the illuminated surface (5) at least partially diffusely scatters incident light.

19. Method according to claim 18, wherein the illuminated surface (5) comprises one of the bottom side (5) of a bottle closure (8), the liquid level (5), and the bottom side (5) of foam (19) in the bottle.

20. Method according to claim 16, and optically magnifying the illuminated bottom side of the surface (5) by an optical device (8) for recording an image.

21. Method according to claim 16, and arranging the image of the bottom of the bottle (6) by a lens (18) through the camera (3).

22. Method according to claim 21, and arranging the illuminated surface (5) to be one of substantially in or a short distance behind the focal plane of the lens (18).

23. Method according to claim 16, wherein the image is recorded from below the bottom of the bottle (6), and the illuminated surface (5) is located above the bottom of the bottle (6).

24. Method according to claim 16 and illuminating the illuminated surface (5) from at least two sides.

25. Method according to claim 16, and illuminating the illuminated surface (5) substantially at an angle and from below.

26. Method according to claim 16, and additionally illuminating the bottle (2) with an additional illumination device (11) from above.

27. Method according to claim 16, and electronically evaluating the recorded images. (2) when it is at least one of filled or closed.

28. Method according to claim 16, wherein the bottles (2) are continuously fed to and removed from an inspection device (1).

* * * * *

UNITED STATES PATENT AND TRADEMARK OFFICE
CERTIFICATE OF CORRECTION

PATENT NO. : 7,057,718 B2
APPLICATION NO. : 10/297909
DATED : June 6, 2006
INVENTOR(S) : Rainer Kwirandt It is certified that error appears in the above-identified patent and that said Letters Patent is hereby corrected as shown below:

At Column 10, lines 27-28, "bottle." should be -- bottle (2) when it is at least one of filled or closed. --.

At Column 10, lines 60-61, "images. (2) when it is at least one of filled or closed." should be -- images. --.

Signed and Sealed this

Tenth Day of April, 2007

JON W. DUDAS
*Director of the United States Patent and Trademark Office*